(12) United States Patent
Gilat

(10) Patent No.: US 8,110,564 B2
(45) Date of Patent: *Feb. 7, 2012

(54) BILE ACID OR BILE SALT FATTY ACID CONJUGATES

(75) Inventor: Tuvia Gilat, Tel-Aviv (IL)

(73) Assignee: Galmed International Limited, B'Kara (MT)

( * ) Notice: Subject to any disclaimer, the term of this patent is extended or adjusted under 35 U.S.C. 154(b) by 24 days.

This patent is subject to a terminal disclaimer.

(21) Appl. No.: 12/361,291

(22) Filed: Jan. 28, 2009

(65) Prior Publication Data

US 2009/0149537 A1    Jun. 11, 2009

Related U.S. Application Data

(63) Continuation of application No. 10/474,032, filed on Oct. 10, 2003, now Pat. No. 7,501,403.

(30) Foreign Application Priority Data

Apr. 17, 2001    (IL) .......................................... 142650
Apr. 15, 2002    (WO) ........................ PCT/IL02/00303

(51) Int. Cl.
*A61K 31/56* (2006.01)

(52) U.S. Cl. ..................................................... 514/182

(58) Field of Classification Search ................... 514/182
See application file for complete search history.

(56) References Cited

U.S. PATENT DOCUMENTS

| 3,856,953 | A | 12/1974 | Saltzman |
| 3,859,437 | A | 1/1975 | Weigand |
| 4,439,366 | A | 3/1984 | Scolastico et al. |
| 4,440,688 | A | 4/1984 | Scolastico et al. |
| 5,278,320 | A | 1/1994 | Monaghan |
| 5,641,767 | A | 6/1997 | Wess et al. |
| 6,384,024 | B1 | 5/2002 | Gilat et al. |
| 6,395,722 | B1 | 5/2002 | Gilat et al. |
| 6,576,660 | B1 * | 6/2003 | Liao et al. ..................... 514/456 |
| 6,589,946 | B2 | 7/2003 | Gilat et al. |
| 6,620,821 | B2 | 9/2003 | Robl |
| 2003/0153541 | A1 * | 8/2003 | Dudley et al. ................. 514/171 |

FOREIGN PATENT DOCUMENTS

| EP | 1379254 | 1/2004 |
| JP | 61-64701 | 4/1986 |
| JP | 2006-306800 | 11/2006 |
| WO | WO-99/22728 | * 5/1999 |
| WO | WO99/52932 | 10/1999 |
| WO | WO2004/001002 | 12/2003 |

OTHER PUBLICATIONS

Reddy et al., "Dietary fenugreek seed regresses preextablished cholesterol gallstones in mice." Canadian Journal of Physiology and Pharmacolocy, 87(9), 684-693, 2009.*
Mendez-Sanchez et al., "Cholesterolosis is not associated with high cholesterol levels in patients with and without gallstone disease." Journal of clinical gastroenterology, 25(3), 518-521, 1997.*
St. George et al., "Spontaneous obesity and increased bile saturation in the ground squirrel." The Journal of surgical research, 55(3), 314-316, 1993.*
Smit et al., "Successful dissolution of cholesterol gallstone during treatment with pravastatin." Gastroenterology, 103(3), 1068-1070, 1992.*
Yamaguchi et al., "Effect of dietary fats on serum and aortic lipid levels of mice fed a high-cholesterol diet: a distinct correlation between linoleic acid intake and the lipid changes." Nippon yakurigaku zasshi. Folia pharmacologica Japonica, 91(2), 61-69, 1988.*
Jaskiewicz et al., "A comparison of the effects of soybean protein and casein on bile composition cholelithiasis and serum lipoprotein lipids in the vervet monkey cercopithecus-aethiops." British Journal of Nutrition, 58(2), 257-264, 1987.*
Gilat, T., et al., "Fatty Acid Bile Acid Conjugates (FABACs)—New Molecules for the Prevention of Cholesterol Crystallisation in Bile," Gut, 48:1 (2001) 75-79.
Gilat, T., et al., "Arachidyl Amido Cholanoic Acid (Aramchol) is a Cholesterol Solubilizer and Prevents the Formation of Cholesterol Gallstones in Inbred Mice," Lipids, 36:10 (2001) 1135-1140.
Goodman and Gilman, 7th Edition, Chaper 34, pp. 827-829, 1985.
Fujino et al., Short Comm., Japan J. Pharmacol., vol. 46, pp. 421-423, 1988.
Saland et al., Anat. Rec., vol. 194, pp. 113-123, 1979.

* cited by examiner

*Primary Examiner* — Barbara P Badio
(74) *Attorney, Agent, or Firm* — Winston & Strawn LLP

(57) ABSTRACT

The present invention relates to the use of a bile acid or bile salt fatty acid conjugate of general formula II

Figure 1A:
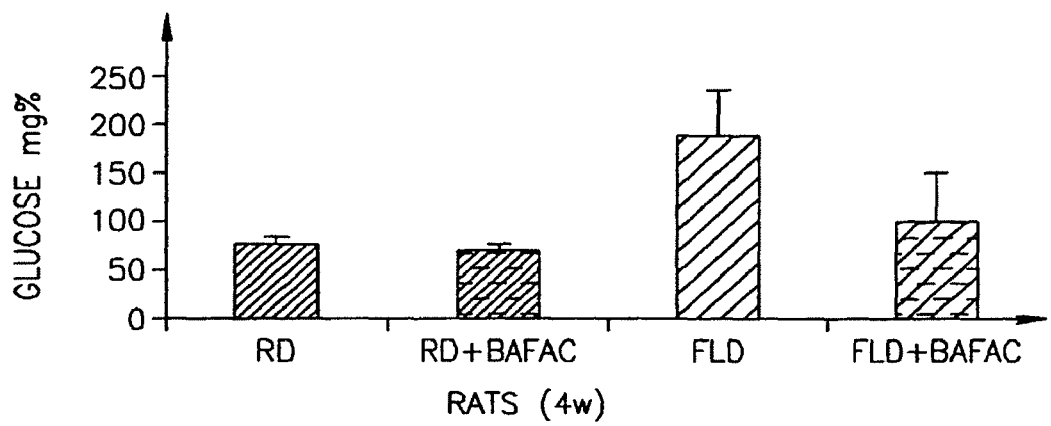

W—X-G in which G is a bile acid or bile salt radical, which, if desired, is conjugated in position 24 with a suitable amino acid, W stands for one or two fatty acid radicals having 14-22 carbon atoms and X stands for a suitable bonding member or for a direct C=C bond between said bile acid or bile salt radical and the fatty acid(s) or of a pharmaceutical composition comprising same for the reduction of Cholesterol in blood, for the treatment of Fatty Liver, Hyperglycemia and Diabetes.

6 Claims, 2 Drawing Sheets

BILE ACID OR BILE SALT FATTY ACID CONJUGATES

This application is a continuation of U.S. application Ser. No. 10/474,032 filed Oct. 10, 2003, now U.S. Pat. No. 7,501,403.

The present invention relates to new uses of certain bile acid or bile salt fatty acid conjugates.

From Israeli Patent Application No. 123.998 there are known bile acid or bile salt fatty acid conjugates [BAFAC I] of general formula I

W-X-G in which G is a bile acid or bile salt radical, which if desired, is conjugated in position 24 with a suitable amino acid, W stands for one or two fatty acid radicals having 18-22 carbon atoms and X stands for a NH bond between said bile acid or bile salt radical and the fatty acid(s).

From said specification there is known the use of the compounds of general formula I and of pharmaceutical compositions comprising same for dissolving cholesterol gallstones in bile, preventing the occurrence or recurrence of said gallstones, and in reducing or preventing arteriosclerosis. There are also known methods for the treatment of said diseases.

It has now surprisingly been found that BAFACS and pharmaceutical compositions comprising same in which W stands for one or two fatty acid radicals having 14 -22 carbon atoms and X stands for a suitable bonding member or for a direct C=C bond between said bile acid or bile salt radical and the fatty acid[s] (being compounds of general formula II; hereinafter called BAFACS II) and pharmaceutical compositions comprising same, have additional uses, namely they can be used:

a. for the reduction of cholesterol concentration in blood;
b. for the treatment of fatty liver; and
c. for the treatment of hyperglycemia and diabetes.

Said BAFACS and pharmaceutical compositions comprising same can also be used in the treatment of said diseases.

The bond has to be a solid bond that is not substantially deconjugated by intestinal and/or bacterial enzymes during the process of absorption. An ester bond is thus not suitable since it is easily deconjugated. The bond stands in particular for NH but may also stand for other suitable bonding members, e.g. S, P, O-ether, etc.

The bond can be in the alpha or beta configuration and can be attached in various positions of the bile acid molecule, positions 3, 6, 7, 12 and 24 being preferred.

The diseases concerned, the history of the treatment thereof and the new use for the treatment thereof are explained hereinafter:

A. Reduction of Cholesterol Concentration in Blood

Hypercholesterolemia is deleterious to health. It is a causative factor in several major disease processes such as ischemic heart disease, myocardial infarction, peripheral vascular disease, possibly stroke, etc. Reduction of cholesterol concentration in blood is beneficial or preventive in some of said diseases. Current medical treatment of hypercholesterolemia is aimed at reducing endogenous cholesterol synthesis in the liver. The statins used for this purpose inhibit the enzyme HMG CoAReductase. However, a major portion of body cholesterol originates from dietary cholesterol. Diet restrictions are notoriously ineffective. Ion exchange resins have also been used to bind bile acids (products of cholesterol catabolism) and sequester them in the intestinal lumen leading to their fecal excretion. They have some effect on blood cholesterol but also important side effects which limit their use.

It has now been shown that BAFACs II reduce diet induced hypercholesterolemia in several animal species even as the animals continue to consume the high cholesterol, high fat diet.

B. Treatment of Fatty Liver

Fatty liver is one of the most common liver diseases today. It is due to excessive accumulation of fat in the liver. It is demonstrated histologically by the presence of variable amounts of micro and/or macro vesicular fat droplets in the liver tissue. Fatty liver can be caused by drugs, chemicals, diseases, bacteria, etc. but the main cause is excessive dietary intake leading to (mainly truncal) obesity.

Due to the increasing prevalence of overweight in affluent societies the prevalence of fatty liver is rising. Fatty liver may progress to steatohepatitis and cirrhosis with the attendant morbidity and mortality.

The best treatment for diet induced fatty liver is sustained weight loss. As is, however, well known this is rarely achieved.

It has now been discovered that BAFACs II can reduce and prevent fatty liver. This has also been demonstrated during continuation of the excessive dietary intake in several animal species.

C. Treatment of Hyperglycemia and Diabetes

Diabetes mellitus is a disorder of carbohydrate (glucose) metabolism. It is schematically divided into type 1, insulin dependent diabetes mellitus (IDDM) characterized by insulin deficiency and type 2, not insulin dependent diabetes mellitus (NIDDM) in which there is mainly insulin resistance. NIDDM is often associated with obesity and/or fatty liver. There are also other causes of hyperglycemia. Treatment of diabetes mellitus involves diet, insulin injections and/or oral hypoglycemic drugs. The aim of therapy is to normalize blood glucose levels. Diabetes, particularly poorly controlled diabetes leads to severe complications.

It has now been discovered that BAFACs reduce and normalize blood glucose levels in animal models of IDDM and NIDDM.

The present invention will now be described with reference to the following Examples and Figs. without being limited to them.

In said Examples the "regular diet" used had the following composition:

Carbohydrates 50%, Protein 21%, Fat 4% with mineral, fiber, and vitamin supplements (manufactured by Koffolk, Petach Tiqwa, Israel).

Figure 1B:
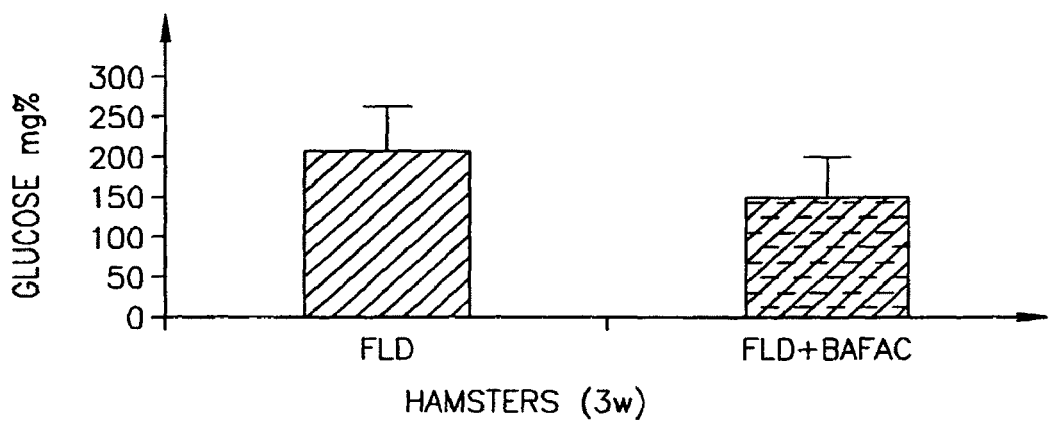
Figure 1C:
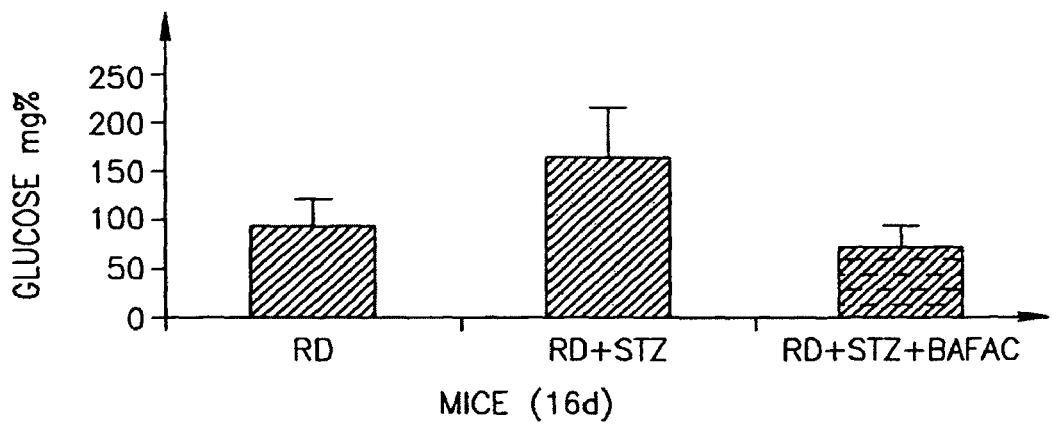
Figure 2:
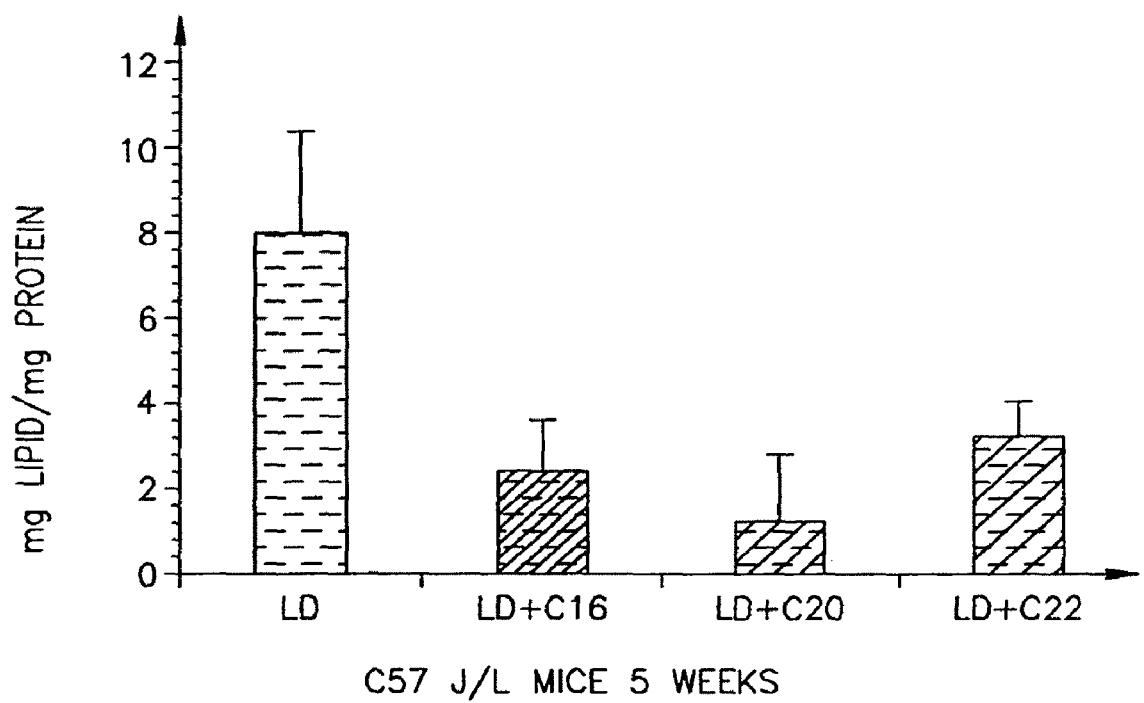

In the Figures,

FIGS. 1A, 1B and 1C show fasting blood glucose concentrations in rodents on different regimens with or without BAFAC (150 mg/kg/day), i.e.:

FIG. 1A for Rats (4w)
FIG. 1B for Hamsters (3w)
FIG. 1C for Mice (16d) and
FIG. 2 shows the lipid/protein ratio in the liver of inbred C57 J/L mice fed a high fat diet +/−BAFAC (150 mg/kg/day) for five weeks.

EXAMPLE 1

1. Hamsters Male

Golden Syrian Hamsters-(Anilab, Rehovot, Israel) 4-6 weeks old weighing 90-110 gm were used. They were fed a lithogenic diet(No. 1) consisting of their regular diet supplemented with (w/w) cholesterol 1%, Palmitic Acid 1.2%, Corn Oil 2% (modified from. Ayyad et al., Lipids, 1992;27:993-998 )for 10 weeks. Half of the animals were given in addition 3β-arachidylamido-7α,12α-dihidroxy-5β-cholan-24-oic acid at a dose of 150 mg/kg/day suspended in saline, by intragastric gavage. The control animals were similarly given an equal volume of saline. After ten weeks the animals were anesthetized, heart blood was drawn for analysis. The liver and other organs were removed. Serum cholesterol levels were determined by autoanalyzer.

2. Mice

Inbred C57 J/L male mice (Jackson Lab., Maine, USA) 4-6 weeks old weighing 20-25 gm were used. They were given their regular diet supplemented with (% w/w) Butter fat 15, Cholesterol 1, Cholic Acid 0.5, Corn Oil 2 (modified from Khanuia et al., *Proc. Natnl. Acad. Sci. USA* 1995; 92:7729-33) for 4-8 weeks.(Lithogenic diet #2) Half of the group were given 3β-arachidylamido-7 α,12α-dihidroxy-5β-cholan-24-oic acid at a dose of 150 mg/kg/day suspended in saline by intragastric gavage. The other half were similarly given an equal volume of saline. After 4-8 weeks the animals were anesthetized, heart blood was drawn for analysis. The liver and other organs were removed. Serum cholesterol levels were determined by autoanalyzer.

Another group of C57 J/L male inbred mice (Jackson Laboratories, Maine, USA) 4-6 weeks old weighing 20-25 gm. were given a lithogenic diet (No. 2) for 8 weeks and then a regular diet for another 8 weeks. During the 8 weeks of the regular diet part of the animals were given 3β-arachidylamido-7α,12α-dihidroxy-5β-cholan-24-oic acid by intragastric gavage at a dose of 150 mg/kg/day. After a total of 16 weeks the animals were anesthetized, heart blood was drawn for analysis. Liver and other organs were removed. Serum cholesterol levels were analyzed as above. A third group of animals were given a regular diet throughout the 16 weeks and then similarly analyzed.

The number of animals in each group and the results are given in the following Table 1

TABLE 1

Serum Cholesterol (mg %) of Test Animals (mean + StD)

| Animals | Diet | Duration (W) | n | Diet Only | n | Diet + BAFAC II |
|---|---|---|---|---|---|---|
| Mice, inbred C57 J/L | Lithogenic 2 | 4 | 5 | 270 (21.7) | 5 | 143 (19.8) |
| Mice, inbred C57 J/L | " | 6 | 6 | 274 (4.1) | 7 | 125 (10.8) |
| Mice, inbred C57 J/L | " | 8 | 5 | 264 (5.8) | 5 | 139 (0.7) |
| Hamsters, Golden Syrian | Lithogenic 1 | 10 | 5 | 257 (32.7) | 5 | 202 (59.6) |
| Mice, inbred C57 J/L | Lithogenic 2 then regular | 8 } 16 8 } | 6 | 101 (10.1) | 7 | 65 (6.8) |
| " | Regular only | 16 | 4 | 81 (5.5) | | |

The data given in Table 1 show that the BAFACs II markedly reduce blood cholesterol levels in numerous groups of mice and hamsters.

EXAMPLE 2

Histologic Examination Method

The presence of fatty liver was evaluated by a pathologist unaware of the treatments, scoring coded slides in a blinded manner.

The scoring system was as follows:

| 0 | No fatty liver | |
| 1 | Minimal fatty liver | <5% of liver surface affected |
| 2 | Mild fatty liver | 5-<25% of liver surface affected |
| 3 | Marked fatty liver | 25-50% of liver surface affected |
| 4 | Severe fatty liver | >50% of liver surface affected |

1. Hamsters

Golden Syrian Male Hamsters (Anilab, Rehovot, Israel) 4-6 years old weighing 90-110 gm were used. They were fed a lithogenic diet (No 1). Half of the animals were given in addition 150 mg/kg/day of 3β-arachidylamido-7α,12α-dihidroxy-5β-cholan-24-oic acid. The compound was given suspended in saline, by intragastric gavage. Control animals were similarly given saline only. After 10 weeks the animals were anesthetized and sacrificed. The liver and other organs were removed and placed in formaline for histologic examination.

2. MICE

C57 male inbred mice (Jackson Lab., Maine, USA) 4-6 weeks old weighing 20-25 gm were used. They were fed a "Western" diet (George et.al. *Circulation* 2000, 102:1822-27) containing cholesterol 1.5 gm/kg and Fat 42%, Carbohydrates 43%, and Protein 15% (as % of calories). Half were given in addition 150 mg/kg/day of 3β-arachidylamido-7α,12α-dihidroxy-5β-cholan-24-oic acid suspended in saline by intragastric gavage. The other half were similarly given saline only. After 4 weeks the animals were anesthetized and sacrificed. Liver and other organs were removed and placed in formaline prior to histologic examination The number of animals in each group and the histologic results are given in the following Table 2.

TABLE 2

Fatty Liver Scores of Test Animals

| Animals | Diet | Duration (W) | n | Control (scores) 0 | 1 | 2 | 3 | 4 | mean | n | +BAFAC (scores) 0 | 1 | 2 | 3 | 4 | mean |
|---|---|---|---|---|---|---|---|---|---|---|---|---|---|---|---|---|
| Hamsters, Golden Syrian | Lithogenic 1 | 10 | 7 | | | | | 7 | 4a | 7 | 6 | 1 | | | | 0.28 |

TABLE 2-continued

Fatty Liver Scores of Test Animals

| Animals | Diet | Duration (W) | Control (scores) | | | | | | +BAFAC (scores) | | | | | | |
|---|---|---|---|---|---|---|---|---|---|---|---|---|---|---|---|
| | | | n | 0 | 1 | 2 | 3 | 4 | mean | n | 0 | 1 | 2 | 3 | 4 | mean |
| Mice C57 J/L Inbred | Western | 4 | 10 | 1 | 3 | 6 | | | 1.5b | 14 | 12 | 1 | | | 1 | 0.35 | aMicrovesicular fat
bMixed (micro and macrovesicular) fat

The data in said Table 2 show that BAFACS reduce and/or prevent fatty liver.

EXAMPLE 3

The effects of BAFACs on fasting blood glucose were tested in 3 animal species: Hamsters, Rats and Mice. The animals were kept on regular or high fat diets (as specified). In each group half of the animals received a daily BAFAC dose (150 mg/kg) dispersed in 0.5 ml of saline by gavage. The other half received similarly, by gavage, an equal volume of saline only. All animals were kept on a 12 hr day/night cycle at 22° C. throughout the experiment. They had access to water ad libidum 1. Hamsters Golden Syrian male hamsters 4 weeks old (90-100 gm) were fed a fatty liver diet consisting of cholesterol (1%), palmitic acid (1.2%), butter (6%), lard (10%), and corn oil (2%) added (w/w) to their regular diet. Blood glucose was measured at sacrifice in the fasting state after 3 weeks of the trial. There were 5 control and 5 test animals.

2. Rats

Wistar male rats 4 weeks old (100-120gm) were fed a regular chow diet or a high fat diet enriched with lard (10%), cholesterol (2.5%) and cholic acid (0.5%) (w/w). Blood and organ samples were obtained after sacrifice (in the fasting state) after 4 weeks of the trial. Half of the animals in each group were given BAFAC 150 mg/kg; the others were given an equal volume of saline. There were 7 rats in the control and test groups on a regular diet and 6 rats in each group given a high fat diet.

The hamsters and rats on the high fat diets developed fatty liver (confirmed by chemical measurement of liver fat), a high fasting blood glucose, and represented models of NIDDM.

3. Mice

ICR male mice, 4 weeks old (approx. 20 gm) were fed a regular diet. Streptozotocin 200 mg/kg was injected i.p. on the first day of the experiment. (This induced damage to the islet cells of the pancreas and simulated IDDM). Fasting blood glucose was obtained from sacrificed animals after 16 days of the trial. There were 3 groups of 7 animals each. Controls—regular diet only. Streptozotocin (Stz) treated animals receiving saline only by gavage and streptozocin treated animals receiving 150 mg/kg/day of BAFAC by gavage. The BAFAC used in all these hyperglycemia studies was a conjugate of arachidic and cholic acid (at position 3) using an amide bond (C-20 BAFAC, Aramchol).

The results of the 3 studies are shown in FIGS. 1A, 1B and 1C. (RD—Regular diet, FLD—Fatty Liver Diet, Stz=Streptozotocin.)

It can be seen that BAFAC supplementation markedly reduced fasting blood glucose in all test animals. Blood glucose was reduced in animals with fatty liver (Hamsters and Rats)—representing NIDDM as well as in the streptozotozin treated mice representing IDDM. BAFACs had no effect on blood glucose in rats on a normal diet (with no hyperglycemia or fatty liver)

EXAMPLE 4

Inbred C57 J/L mice, 4 weeks old and weighing approx. 20 gm (Jackson Lab. Maine, USA) were used. They were fed for 5 weeks a high fat lithogenic diet consisting of: Cholesterol 1%, Cholic Acid 0.5%, lard 10%, bufter 6%, palmitic acid 1.2% and corn oil 2% added (w/w) to their regular diet. In addition to the diet the animals were given daily, by gavage, either a BAFAC(150 mg/Kg) suspended in saline or an equal volume of saline only. The BAFACs were conjugates of cholic acid (at position 3) with either Palmitic Acid (C-16) or Arachidic Acid (C-20) or Behenic Acid (C-22) using an amide bond. The controls (n=5) received saline, the test animals received either the C-16 conjugate (n=5), the C-20 conjugate (n=5) or the C-22 conjugate (n=3). After 5 weeks, following an overnight fast, the animals were anesthetized using ketamine, the liver was removed, and the animals were sacrificed by ketamine overdose. A 0.5 gm sample of liver was homogenized in 5 ml of buffered saline. Liver lipids were extracted from the homogenate by the Folch method using chloroform: methanol (2:1, vol/vol). Half a ml of the homogenate were extracted in 5 ml of the Folch solution. After evaporation of the solvent the lipids were weighed and reevaporated several times until constant weight was obtained The proteins were quantified in another aliquot of the homogenate according to the method of Bradford (Bradford M. M., Annal. Biochem. 1976, 72:248)

The lipid protein ratio (mg/mg) was calculated. The results for each group are given as means (+St. Dev.) The group values were:

Controls 7.9+/−2.32 , C-16 BAFAC 2.25+/−1.20 , C-20 BAFAC 1.44+/−1.18, and C-22 BAFAC 3.00+/−1.08. The results are illustrated in FIG. 2.

The data show that the effects claimed are exercised by several conjugates, some of them almost as potent as the C-20 conjugate used in examples 1, 2 & 3.

What is claimed is:

1. A method for reducing cholesterol levels in the blood of a subject in need thereof as determined by analyzing the subject's serum cholesterol level, said method comprising the step of administering to the subject a BAFAC of general formula II

W—X-G in which G is a bile acid or bile salt radical, which is optionally conjugated in position 24 with a suitable amino acid, W stands for one or two fatty acid radicals, each having from 14-22 carbon atoms, and X is a direct C=C bond between G and each W, with the BAFAC administered in an amount sufficient to lower the subject's serum cholesterol levels.

2. The method according to claim 1, wherein in the compound of general formula II the fatty acid is selected among behenylic acid, arachidylic acid and stearic acid.

3. The method according to claim 1, wherein in the compound of general formula II, W is one fatty acid radical.

4. A method for reducing diet induced hypercholesterolemia caused by intake of a high cholesterol diet in a subject in need thereof as determined by analyzing the subject's serum cholesterol level, said method comprising the step of administering to the subject a BAFAC of general formula II

W—X-G in which G is a bile acid or bile salt radical, which is optionally conjugated in position 24 with a suitable amino acid, W stands for one or two fatty acid radicals, each having from 14-22 carbon atoms, and X is a direct C=C bond between G and each W.

5. The method according to claim 4, wherein in the compound of general formula II the fatty acid is selected among behenylic acid, arachidylic acid and stearic acid.

6. The method according to claim 4, wherein in the compound of general formula II, W is one fatty acid radical.

* * * * *

UNITED STATES PATENT AND TRADEMARK OFFICE
CERTIFICATE OF CORRECTION

PATENT NO. : 8,110,564 B2  Page 1 of 1
APPLICATION NO. : 12/361291
DATED : February 7, 2012
INVENTOR(S) : Gilat It is certified that error appears in the above-identified patent and that said Letters Patent is hereby corrected as shown below:

Title Page:
Item (63) Related U.S. Application Data:
After "10/474,032," delete "filed on Oct. 10, 2003," and insert -- filed as application No. PCT/IL02/00303 on Apr. 15, 2002 --. The related U.S. application data will then correctly appear as "Continuation of application No. 10/474,032, filed as application No. PCT/IL02/00303 on Apr. 15, 2002".

Item (30) Foreign Application Priority Data:
Delete "Apr. 15, 2002 (WO) ...............PCT/IL02/00303".

Item (56) References Cited, OTHER PUBLICATIONS:
Reddy et al. reference: change "preextablished" to -- preestablished --; and change "Pharmacolocy" to -- Pharmacology --.
Saland et al. reference: change "113-123" to -- 113-124 --.

Item (57) ABSTRACT:
In line 3, change "W—X-G" to -- W-X-G --.

Column 1:
Line 6, delete "403." and insert -- 403, which is a 371 of PCT/IL02/00303 filed April 15, 2002. --.

Column 6:
Line 62 (claim 1, line 6), change "W—X-G" to -- W-X-G --.

Signed and Sealed this
Eighth Day of May, 2012

David J. Kappos
*Director of the United States Patent and Trademark Office*